United States Patent
Shastri et al.

(10) Patent No.: US 9,441,051 B2
(45) Date of Patent: Sep. 13, 2016

(54) MATRICES COMPRISING MODIFIED POLYSACCHARIDES AND MODIFIED POLYSACCHARIDES

(71) Applicant: Albert Ludwigs Universität Freiburg, Freiburg (DE)

(72) Inventors: V. Prasad Shastri, Freiburg (DE); Aurelien Forget, Freiburg (DE); Florian Mießmer, Frieburg (DE)

(73) Assignee: ALBERT LUDWIGS UNIVERSITÄFREIBURG, Freiburg (DE)

(*) Notice: Subject to any disclaimer, the term of this patent is extended or adjusted under 35 U.S.C. 154(b) by 0 days.

(21) Appl. No.: 14/085,244

(22) Filed: Nov. 20, 2013

(65) Prior Publication Data

US 2014/0147407 A1    May 29, 2014

Related U.S. Application Data

(60) Provisional application No. 61/729,982, filed on Nov. 26, 2012.

(51) Int. Cl.
| | | |
|---|---|---|
| *C08B 37/00* | (2006.01) | |
| *A61K 8/73* | (2006.01) | |
| *C08B 37/08* | (2006.01) | |
| *A61Q 5/00* | (2006.01) | |
| *A61Q 19/00* | (2006.01) | |

(52) U.S. Cl.
CPC .............. *C08B 37/00* (2013.01); *A61K 8/73* (2013.01); *C08B 37/003* (2013.01); *C08B 37/0039* (2013.01); *C08B 37/0042* (2013.01); *C08B 37/0072* (2013.01); *C08B 37/0075* (2013.01); *A61K 2800/10* (2013.01); *A61Q 5/00* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 4,973,683 A | * | 11/1990 | Lindgren | 536/120 |
| 6,426,315 B1 | | 7/2002 | Bergstrom et al. | |
| 2003/0103916 A1 | * | 6/2003 | Imanaka et al. | 424/62 |
| 2006/0029599 A1 | * | 2/2006 | Kaisheva et al. | 424/133.1 |

OTHER PUBLICATIONS

Youping et al., "Preparation of Agarose Sulfate and Its Antithrombogenicity", J. Wuhan Uni. Tech. Mater. Sci. Ed., 2012, pp. 110-114.*
Fort et al., J. Am. Chem. Soc., 2000, 122(23), pp. 5429-5437.*
Suflet et al., React. Funct. Poly., 2006, vol. 66, pp. 1240-1249.*
European search report received in connection with European application No. 12194226.2; dtd Mar. 1, 2013 (8 pages).
Jie et al., "Preparation of Agarose Sulfate and Its Antithrombogenicity", Journal of Wuhan University of Technology-Mater. Sci. Ed., vol. 27, Issue 1, pp. 110-114 (Feb. 2012).
Forget et al., "Modification of Polysaccharides for Mechanically Tunable Synthetic ExtraCellular Matrices", Institute for Macromolecular Chemistry, University of Freiburg, Germany.

* cited by examiner

*Primary Examiner* — Brian Gulledge
(74) *Attorney, Agent, or Firm* — The Marbury Law Group, PLLC

(57) ABSTRACT

The present invention discloses a matrix comprising a modified primary hydroxyl groups containing polysaccharide comprising repeating disaccharide units wherein in at least part of the disaccharide units the primary hydroxyl group is replaced by functional groups selected from halide groups or groups comprising sulfur or phosphorus atoms, like e.g. sulfate groups, sulfonate groups, phosphonate groups and phosphate groups.

19 Claims, 2 Drawing Sheets

Figure 1   ESEM images of 2% w/v freeze dried gels
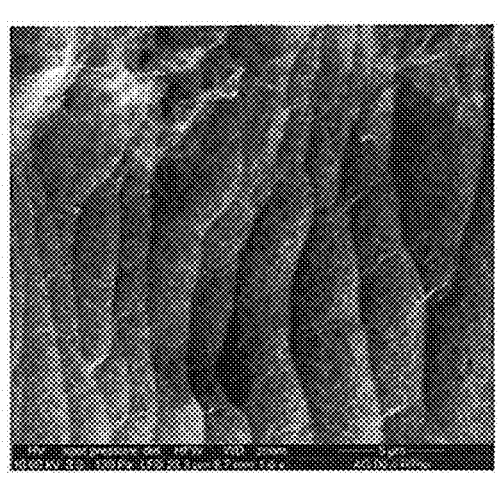
unmodified agarose
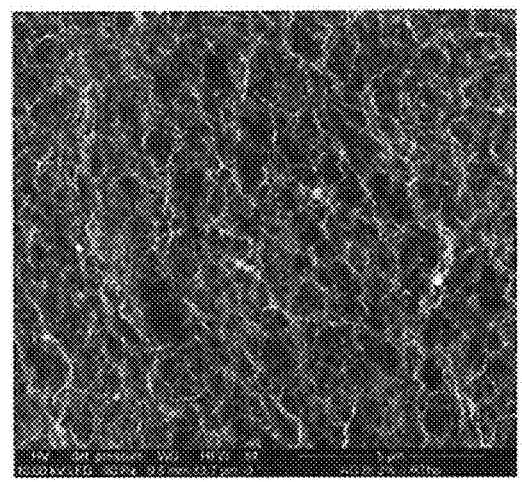
brominated-agarose
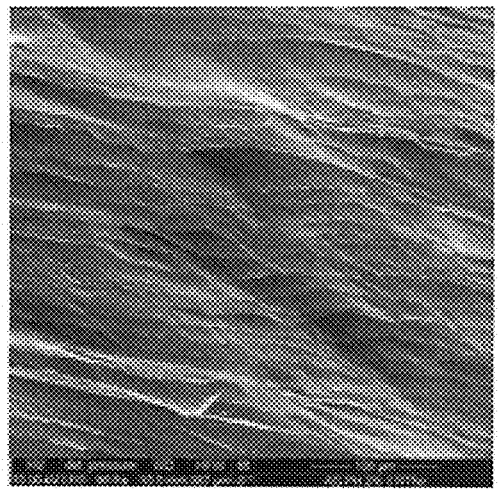
phosphorylated agarose
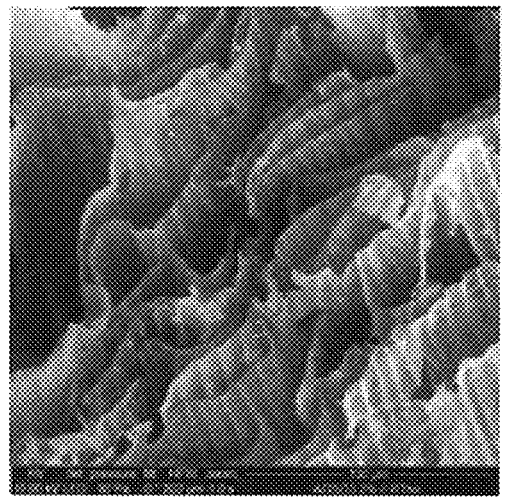
agarose sulfate Figure 2    AFM phase images of the surface of 2 % w/v wet hydrogel
unmodified agarose
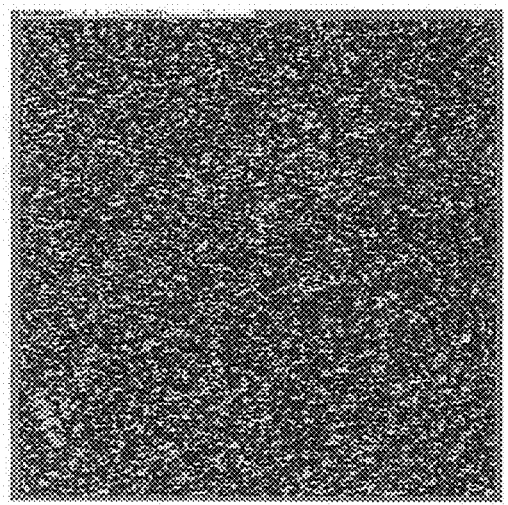
Br-agarose
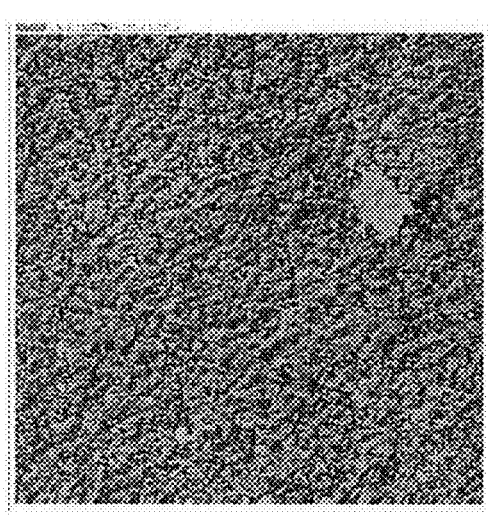
phosphorylated-agarose
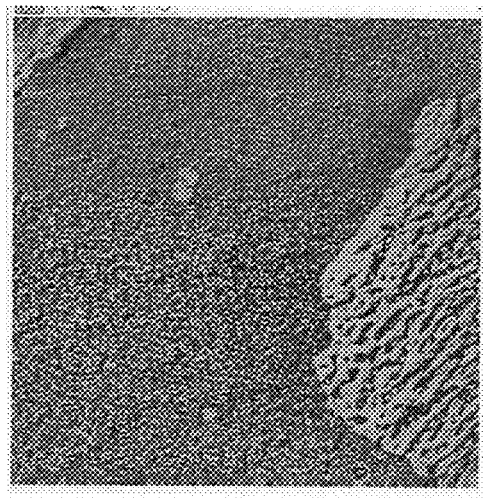
agarose sulfate
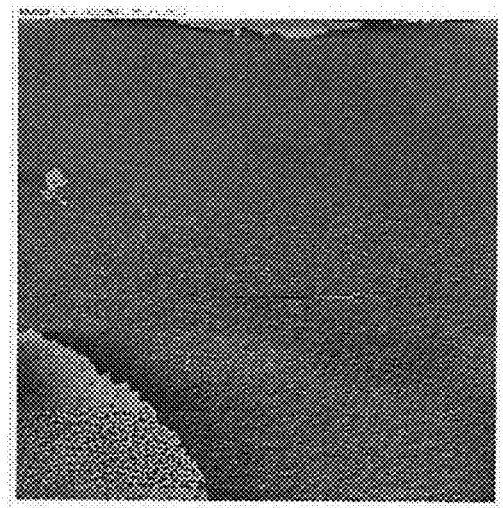

MATRICES COMPRISING MODIFIED POLYSACCHARIDES AND MODIFIED POLYSACCHARIDES

CROSS-REFERENCE TO RELATED APPLICATIONS

This patent application is a non-provisional application which claims benefit of U.S. Provisional Patent Application No. 61/729,982, filed Nov. 26, 2012, the complete disclosure of which, including page 34, is incorporated herein by reference in its entirety.

FIELD OF THE INVENTION

The present invention relates to matrices comprising a modified polysaccharide and the applications of such matrices. The matrixes can be used as scaffold for living cells regenerative implants, plastic surgery implants, in controlled drug release systems or as excipients in drug formulations. In addition thereto, the matrixes of the present invention are suitable for use as a food additive, a component for cosmetic compositions, hair care products, and for other industrial purposes as well as generally in the area of tissue engineering and regenerative medicine and cell encapsulation. In another aspect the present invention relates to novel modified polysaccharides, in particular novel modified agarose.

NOMENCLATURE

In the text of the present application, the nomenclature of amino acids and of peptides is used according to "Nomenclature and symbolism for amino acids and peptides", Pure & Appl. Chem., Vol. 56, No. 5, pp. 595-624, 1984, if not otherwise stated.

The following abbreviations have the meaning as given in the following list, if not otherwise stated:
AFM atomic force microscopy
DNA deoxyribonucleic acid
ECM extracellular matrix
ESEM environmental scanning electron microscopy
MD molecular dynamics
Mn number average molecular weight

BACKGROUND OF THE PRESENT INVENTION

Living cells of higher organisms reside in an environment that is mechanically and biologically well-defined by an extracellular matrix (in the following ECM). Structural and mechanical aspects of the ECM such as stiffness and topography can have a substantial influence on different cell functions like cell growth or differentiation of the cells.

The present invention provides matrices wherein important mechanical and chemical properties of the matrix can be adjusted according to the desired application.

The cell surrounding has been considered in the past decades to be an important piece of the puzzle of organogenesis. It is known that each type of cell builds and evolves in a specific environment that provides the mechanical properties and the nutritional needs of the cell. This environment is called extracellular matrix (ECM). Structural and functional components of the ECM can modulate cell behavior and function and also determine which cell can interact with another in the human body. Nevertheless, most of these intercellular interactions are not fully understood. It has been shown that the properties of the ECM supporting the cell in the human body have many aspects (physical and chemical) that have been shown to impact the cell fate in vitro and in vivo. It has been found that in addition to cell adhesion moieties and growth factors, the physical attributes of a cellular microenvironment namely, stiffness and topography are another important element in dictating and controlling cell fate and function.

Providing a synthetic ECM would be a significant contribution to investigation of such intercellular interaction. Importantly, a model employing such ECM would allow mimicking of human tissues in vitro and be amenable to translation in viva. A further aim of this model is to enable communicating with the body and aid in healing or regeneration of tissues. Injectable, biologically well-defined matrixes with tailor-made and tunable physical properties would be the evolutionary next-step in synthetic niches for cells.

An extracellular matrix (ECM) is usually defined as an assembly of molecules composing the cell surrounding.

In general an ECM is made up of different components that can be classified as:
(1) the soluble molecules, e.g. growth factor and other signaling molecules and
(2) the structural polymers, composed of proteins and polysaccharides that determine the mechanical properties of the tissues.

The term "growth factor" relates to a naturally occurring compound which is capable of stimulating cellular growth, proliferation and differentiation. Preferably, the growth factor is a polypeptide or a protein, for instance, a water-soluble protein.

The term "protein" relates to a polymeric structure which consists of one or several polypeptides. Polypeptides, in turn, consist of amino acid residues joined together by peptide bonds. Preferably, the amino acids of the proteins are L-α-amino acids, whereby proteinogenic amino acids are particularly preferred. It is preferred that proteins acting as components of an extracellular matrix are not water-soluble. The term "peptide sequence" used in the present invention relates to a polypeptide. Preferably, a peptide sequence has between 2 and 50 amino acid residues, particularly preferred between 5 and 20 amino acid residues.

Some synthetic matrixes for use as ECM have already been commercialized. So far four different strategies have been explored to produce synthetic ECMs:
(1) Use of animal protein extracts such as Matrigel® which suffer from a lack of batch-to-batch reproducibility and a poor definition of the components. This leads to difficulties in the interpretation of the results obtained with such ECMs.
(2) Use of synthetic polymers such as degradable polyesters and polyethyleneglycol (or oxide) derivatives, such as diacrylates or methacrylates that can be chemically of photochemcially crosslinked, that although biocompatible are not easy to synthesize and manufacture and additionally, require knowledge in synthetic chemistry to set it up and are also difficult to translate into in vivo clinical settings.
(3) Use of natural components of the ECM such as collagen or hyaluronic acid, which reproduce only one aspect of the natural ECM environment.

As outlined in the review of Tan et al (*Materials* 2010, 3, 1746-1767) various polysaccharides have been suggested as suitable materials for ECMs in the last decades. Prominent among them are hyaluronic acid, alginate acid and chitosan. Hyaluronic acid when modified using long chain alcohols can yield gels that are formed due to physical cross-links established by the aggregations of the hydrophobic alkyl chains in water. Hyaluronic acid can also be gelled using covalent crosslinking. In this case, the hyaluronic acid is oxidized to bear aldehyde groups which are then reacted with N-succinyl modified chitosan or other biopolymers. Subsequently, the crosslinking is induced by diamine through Schiff base formation. Alginic acid can also be processed into gels that can serve as cell supports by ionic crosslinking it with divalent cations $Ca^{2+}$, $Mg^{2+}$, $Ba^{2+}$ or $Sr^{2+}$.

Polysaccharides bearing helical motifs such as e.g. agarose or carrageenan until today have a limited suitability for use in such matrices.

Youping Jie et al., J. of Wuhan University of Technology—Materials Science Ed. Vol. 27, Issue 1, pp 110-114 (2012) disclose the preparation of agarose sulfate by reacting agarose with chlorosulfonic acid in pyridine. The authors outline that the use of agarose in the biomedical field had been limited and that functionalization is necessary to a certain degree to obtain agarose with biological activity. Agarose was sulfated with chlorosulfonic acid/pyridine with formamide as dispersing agent. Agarose with a degree of substitution between 0.17 and 0.43 was obtained and the product is said to be useful as heparin like material in anticoagulation or endothelial regeneration scaffold.

Agarose modified with N-hydroxy succinimide is available as a commercial product from Thermo Scientific and is said to be useful to covalently immobilize antibodies or proteins for use in affinity purification procedures. Particular examples given are improved coupling to human IgG, rabbit IgG and it is also shown that the modified agarose is effective for immunoprecipitation of MAP kinase from HeLa cell lysate.

Shoichet and Luo, Biomacromolecules 2004, 5, 2315-2323 describe the light activated immobilization of biomolecules to agarose for controlled cellular response. Agarose modified with S-(2-nitrobenzyl)cysteine (S-NBC) yielded a modified agarose with appr. 5% S-NBC substitution, which was still soluble and gelable. Irradiation resulted in the loss of the protecting 2-nitrobenzyl groups exposing free sulfhydryl groups which are available for biomolecular coupling. Peptides and proteins could be effectively immobilized. It is outlined that the immobilization of biomolecules to hydrogels is an important tool to control the physical and chemical properties of the gel while at the same time providing bioactive materials for i.a. biomimetic materials.

WO2012/146374 describes extracellular matrices comprising modified polysaccharides in which at least 11% of the primary hydroxyl groups in the polysaccharide have been oxidized to carboxylic acid groups. The matrices can optionally contain unmodified polysaccharides. A preferred polysaccharide is agarose.

Chitanu et al., Carbohydrate polymers 82 (2010), 1271-1277, describe the synthesis and properties of phosphonated dextran. Dextran is a polysaccharide without primary hydroxyl groups and the modification occurs primarily at the secondary hydroxyl group at C-2 in the dextran molecule.

Chitanu et al., Reactive and Functional polymers 66 (2006) 1240-1249 report on the phosphorylation of cellulose wherein a part of the primary hydroxyl groups are converted to phosphonate groups groups.

In both cases phosphonic acid (sometimes also referred to as phosphorous acid) is used as reactant.

It was an object of the present invention to provide materials and matrices based on modified polysaccharides, which can be used for a variety of purposes.

This object is achieved with the matrices in accordance with claim 1.

Preferred embodiments in accordance with the present invention are set forth in the dependent claims and the detailed description hereinafter.

The present invention provides a matrix suitable for various applications. The matrix of the present invention can be used e.g. as a food additive, material for surgery implants, in controlled drug release systems, as lubricant for industrial purposes, for conditioning of liquids, in biomedical device coatings, as excipients in drug delivery formulations, in cell encapsulation and in the area of tissue engineering and regenerative medicine. In addition thereto, the matrixes of the present invention are suitable for use as components of cosmetic compositions, as components of hair care products and for other industrial purposes.

Another aspect of the present invention relates to modified polysaccharides wherein at least 10% of the primary hydroxyl groups have been converted to halide groups, which products are referred to hereinafter as halogenated polysaccharides.

Agarose is a preferred polysaccharide which can be modified in accordance with the present invention.

Halogenated polysaccharides and in particular fluorinated polysaccharides (agarose again being especially preferred as polysaccharide), optionally in combination with unmodified polysaccharides can be advantageously used for hair-care products like styling gels and sprays and the like.

Polysaccharides which comprise halide groups (F, Cl, Br or I) as well as phosphate groups, optionally in combination with unmodified polysaccharides, provide beneficial effects in dental and orthopedic applications.

Another embodiment of the present invention relates to phosphorylated agarose wherein at least 10% of the primary hydroxyl groups have been converted to phosphonate or phosphate groups. Whereas generally the term phosphorylation is used to designate the introduction of phosphate groups into biological materials, in the context of the present invention this term is used for phosphonated as well as for phosphated agarose. The respective modification can be achieved by reaction with phosphonic acid $H_3PO_3$ (yielding the phosphonate modification) or reaction with phosphoric acid $H_3PO_4$ which yields the phosphates. Whereas in phosphonates the valency of phosphorus is three, it is 5 in phosphates. In phosphonates two possible chemical structures can be present which are both encompassed by the term phosphorylated agarose as used herein. The two structures are expected to be different at least concerning the dissociation behaviour. One of the forms should behave like a monobasic acid whereas the other form should behave like a dibasic acid. The two forms are present in a tautomeric equilibrium.

The two tautomeric forms are the following, the lower structure being normally prevalent:

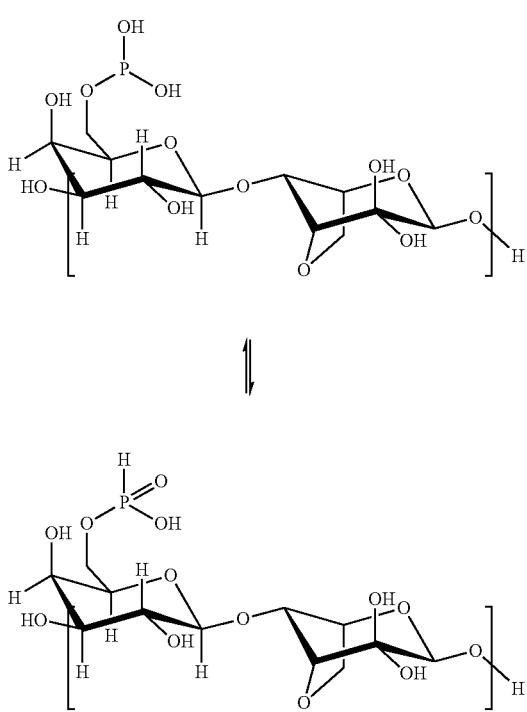

The matrices of the present invention comprise modified polysaccharides comprising repeating disaccharide units wherein at least part of the disaccharide units carry functional groups selected from halide groups or groups comprising sulfur or phosphorus atoms, like e.g. sulfate groups, sulfonate groups, phosphonate groups and phosphate groups.

As used herein, the term "polysaccharide" relates to a polymeric carbohydrate structure, which is formed of repeating units joined together by glycosidic bonds. Preferably, the repeating units are either mono- or disaccharides and the polymeric structure of the polysaccharide is non-branched. It is preferred that the number average molecular weight of the polysaccharide ranges from 10 000 Dalton to 500 000 Dalton, particularly preferred the number average molecular weight of the polysaccharide ranges from 50 000 Dalton to 300 000 Dalton, with a number average molecular weight of the polysaccharide ranging from 80 000 Dalton to 140 000 Dalton being even more preferred.

It is an essential component of the matrix of the present invention to contain at least one modified polysaccharide whereby the modified polysaccharide comprises and preferably consists essentially of or even more preferably consists entirely of repeating disaccharide units. In a preferred embodiment the modified polysaccharide is derived from agarose. In yet another preferred embodiment the modified polysaccharide is derived from fragmented agarose.

Agar, the main source of agarose is a structural polysaccharide of the cell walls of a variety of red algae. Important sources of agar are Gelidiaceae such as *Gelidium amansii*, *Gelidium japonicum*, *Gelidium pacificum*, *Gelidium subcostatum*, *Pterocladia tenuis* and *Acanthopeltis japonica*, red algae belonging to Gracilariaceae such as *Gracilaria verrucosa* and *Gracilaria gigas*, red algae belonging to Ceramiaceae such as *Ceramium kondoi* and *Campylaephora hypnaeoides*. Agar consists of two groups of polysaccharides, namely agarose and agaropectin. Agarose is a neutral, linear polysaccharide with no branching and has a backbone consisting of 1,3-linked β-D-galactose-(1-4)-α-L-3,6 anhydrogalactose repeating units. This dimeric repeating unit, called agarobiose differs from a similar dimeric repeating unit called carrabiose which is derived from carrageenan in that it contains 3,6-anhydrogalactose in the L-form and does not contain sulfate groups.

In accordance with the present invention, dimeric repeating units derived from naturally occurring polysaccharides are chemically modified to obtain halide functional groups or functional groups comprising sulfur or phosphorus atoms.

To obtain a halide modification, the unmodified polysaccharide may be reacted with N-halogenated succinimide in dry dimethylformamide using triphenyl phosphine as catalyst. The following reaction scheme shows this general reaction for agarose as polysaccharide and Br as preferred halide:

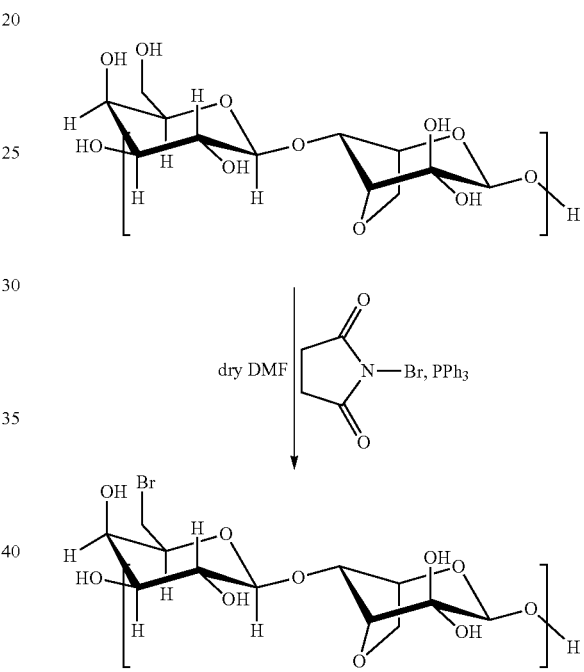

A versatile reagent for the nucleophilic fluorination of primary alcohols is diethyl amino sulfur trifluoride (DAST), which is commercially available e.g. from Sigma Aldrich. DAST has proven to be versatile in a significant number of fluorination of in particular alcohol groups and thus it can be used to obtain the fluorinated polysaccharides in accordance with the present invention. The skilled person will chose the suitable reaction conditions based on his professional knowledge.

Ritter et. al in Current Topics in Drug Discovery and Development 2008, 11(6) 803ff. provide a good review of fluorination reactions with various reagents including DAST and is incorportated by reference in its entirety herewith, The introduction of halides into the backbone of the polysaccharide promotes intra-molecular interaction within the polysaccharide chain.

To obtain a modification with phosphate groups, the polysaccharides may be reacted with phosphoric acid in dry DMSO in the presence of urea in accordance with the following reaction scheme:

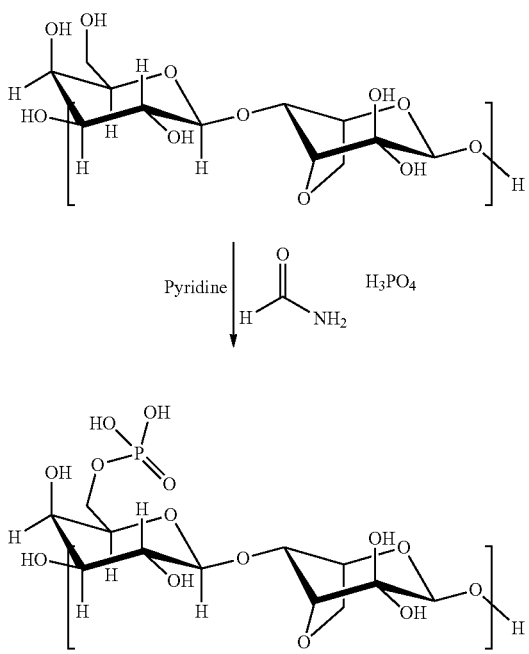

The introduction of sulfate groups may be achieved by reacting the respective polysaccharide with a combination of chlorosulfonic acid and formamide in dry pyridine in accordance with the following reaction scheme (again shown for agarose):

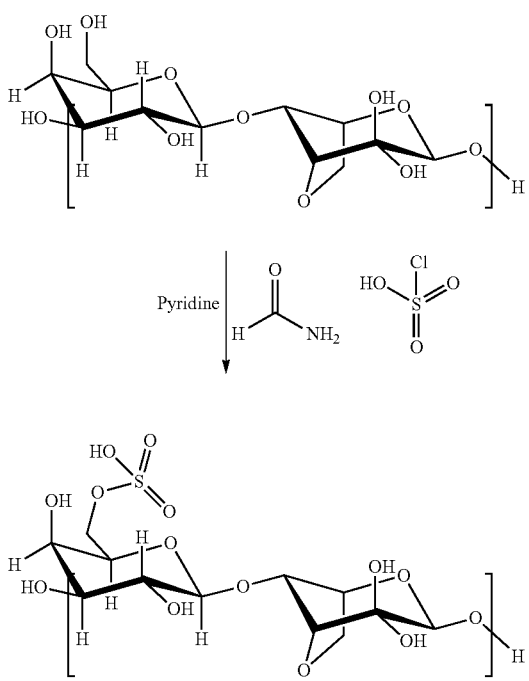

The introduction of charged groups like the sulfate or phosphate groups into the backbone of the polysaccharide impacts the intermolecular chain-chain hydrogen bonding interaction in the polysaccharide chain due to an increase in the electronic repulsion.

Sulfonation appears to eliminate inter-molecular hydrogen bonding to a significant extent.

As outlined in the reaction schemes above, the modification usually occurs at the primary hydroxyl groups of the polysaccharide.

Depending on the chosen reaction conditions it is possible to adjust the degree of modification of the primary hydroxyl groups in the polysaccharide. In accordance with a preferred embodiment at least approximately 5, more preferably at least 10% of the primary hydroxyl groups are modified with the respective halogen or phosphorus or sulfur containing groups. Even more preferably 20 to 99% of the primary hydroxyl groups are modified with a range of 50 to 95% of modification being even more preferred.

Thus, the modification reaction may be carried out in a controlled manner so that only a partial modification of the primary hydroxyl groups of the primary alcohol groups takes place. However, the polysaccharide can also be modified in such a way that about 100% of the primary hydroxyl groups are modified.

The completely or partially modified polysaccharide can be subsequently blended with an unmodified polysaccharide, which may either be the same polysaccharide or another polysaccharide. Since the nature and extent of the chemical modification of the modified polysaccharide can be controlled and the blending ratio with another polysaccharide or the same unmodified polysaccharide can be adjusted it is possible to control the chemical properties of the resulting matrix.

The content of the modified polysaccharide in the matrix of the present invention is in the range of 1-99 wt.-% based on the weight of the entire matrix. In a preferred embodiment the present invention the content of the modified polysaccharide in the matrix is greater than 1 wt.-%, preferably it is greater than 10 wt.-%. It is yet even more preferred that the ratio of the modified polysaccharide in the matrix is greater than 20 wt. %, in particular greater than 50 wt.-%.

One important aspect of the present invention is the shear modulus G' of the matrix. According to the present invention the shear modulus can range from about 10 Pa, which reflects the structure of a nerve tissue to about $10^7$ Pa which corresponds with the shear modulus of cartilage tissues. By blending gels of different extent of chemical modification the nanoscale structure of the gel can be impacted. It has been shown that nanoscale topography influences cell shape, cytoskeletal assembly and function. It is for this reason that the matrix of the present invention can induce changes in mammalian cell shape or mammalian cell function.

The presence of charged moieties like sulfonate or phosphate groups along the backbone of the polysaccharide chain has been observed to interrupt or weaken the chain-chain interaction leading to a decrease of the shear modulus compared to the respective modulus of the unmodified polysaccharide whereas the introduction of halide groups may be used to increase the modulus G'.

The shear modulus of the matrix ranges preferably from 1 Pa to 100 kPa, more preferred from 1 Pa to 50 kPa and in a most preferred embodiment in a range from 10 Pa to 10 kPa, whereby the measurement of the shear modulus is carried out at a temperature of 37° C. as specified below.

The backbone modification of polysaccharides in accordance with the present invention impacts the chain organization of the polysaccharide and as a result leads to a modification of the macrostructure.

Generally, increasing the charge density along the backbone promotes higher order in the structure and the formation of sheet like structures.

The introduction of charged moieties seems to promote the formation of larger domains, which may have a direct impact on the organization of the polysaccharide chains at larger length scales.

The introduction of bromine groups into polysaccharides leads to heterogeneous phase separated structures at the nanoscale which effect may be advantageously used for various applications.

In an especially preferred embodiment agarose wherein the primary hydroxyl group has been modified as outlined before is blended with non-modified agarose.

Agarose is commonly used for separation techniques such as electrophoresis, Gel Permeation Chromatography, High Performance Liquid chromatography but also as a food additive. Recently the use of agarose hydrogel has shown to be useful for engineered ECM. Agarose has been successfully used to engineer cartilage de novo which suggest that further development will offer the possibility to regenerate other tissues. It has been shown that agarose gels induce bone reconstruction in vivo. It has also been shown that it is possible to modify the agarose backbone by oxidizing the primary alcohol group of the D-galactose residue in a highly regioselective manner. This modification enables grafting of molecules on the agarose gel through a carboxylic acid group. Therefore, the matrix of the present invention is highly valuable for biochemical and medical applications.

Experiments have been shown that the polysaccharide hydrogels comprising groups as described before show an excellent cytocompatibility. HeLa and MDA-MB 231 cancer cell lines proliferate normally upon treatment with media that was exposed to a hydrogel with a modified polysaccharide as described before which is an indication of the absence of toxic components.

It has been observed that the modification of the C6 primary hydroxyl group of the D-galactose residue leads to a decrease of shear modulus but also to a weaker gel. The design of new material using agarose has been investigated by creating copolymer of agarose-collagen, or agarose-cellulose, but also by blending agarose with natural polymer of the ECM.

Modified agarose is the preferred component of the matrix of the present invention. Moreover, it is possible to use other polysaccharides of natural origin as component, which can be blended with modified agarose if such component cannot be modified as described above. If the structure of the polysaccharide contains a primary alcohol group the repeating disaccharide units can be modified as described above in more detail for agarose. Other polysaccharides, which can be used in the present invention are listed in Table 1 below. Polysaccharides in cells with bold borders usually comprise disaccharide units having a primary hydroxyl group. Therefore, these polysaccharides can be chemically modified in the manner described above. In particular, preferred polysaccharides used for the matrix of the present invention are hyaluronic acid, heparin sulfate, dermatan sulfate, chondroite sulfate, alginate, chitosan, pullulan, k-carrageenan as shown in the table below. In the most preferred embodiment agarose is used.

| Name | Structure | Orgin | Gelation mechanism |
|---|---|---|---|
| Hyaluronic Acid | 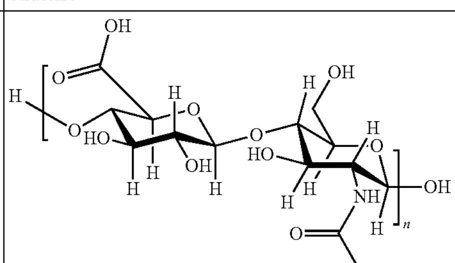 | Mammalian | uses of crosslinker to form a 3D network |
| Heparin sulfate | 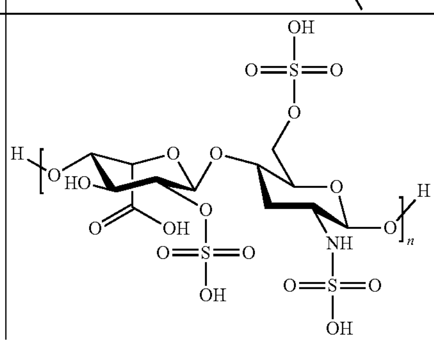 | Mammalian | |

| | | | |
|---|---|---|---|
| Dermatan sulfate | | Mammalian | |
| Chondroite sulfate | | Mammalian | |
| Alginate | | Algae | $Ca^{2+}$ bridges |
| Chitosan | | Marine shell | Repulsion of charges |
| Pullulan | | Fungus | Like cellulose, sheet organization |
| k-Carrageenan | | Algae | helices aggregation |
| Agarose | | Algae | helices aggregation |

In another embodiment of the present invention the matrix contains carrageenans in modified or/and unmodified form. Carrageenans are polysaccharides that are contained in red algae belonging to Gigartinaceae, Solieriaceae, Hypneaceae and the like. K-carrageenan, λ-carrageenan and η-carrageenan are known.

In further preferred embodiments of the present invention the group which is derived from the modification of the primary hydroxyl group, in particular if the modification is a sulfate, a sulfonate or a phosphate group, may be covalently coupled with a peptide sequence. In preferred embodiments the peptide sequence is selected from the group consisting of the cell adhesion sequence arginine-glycine-aspartic acid (RGD), the peptide sequences IKVAV and YIGSR or a protein which is preferably selected from collagen, collagen fragments, fibronectin and mixtures thereof. In yet another embodiment the protein sequence is vitronectin.

In another preferred embodiment the matrix may contain a modification insofar that the modified group is covalently linked to a nucleic acid sequence. The nucleic acid sequence may be single-stranded DNA, double-stranded DNA, single-stranded RNA and siRNA. The linkage between the modified group and nucleic acid can be introduced by a method of click chemistry as known in the prior art. In case single-stranded nucleic acids are linked to the matrix, such single-stranded molecules may hybridize to complementary single-stranded molecules which are linked to other components. This offers the opportunity to easily attach molecules or even whole cells to the matrix.

Depending on the purpose of the use of the matrix it may be particularly helpful to include specific points of fixation into the matrix which can be designed according to the intended use of the matrix.

The present disclosure further describes the ability to change the tertiary structure of polysaccharides in a manner that the roughness, stiffness, thermal gelation behavior and optical feature of the material can be finely tuned to target a specific material, whereby the modification made on the backbone consists in a modification of the primary alcohol group of the polysaccharide backbone as described above.

It was demonstrated that this modification induces a change of organization of the polymer backbone and the effect has been replicated in k-carrageenan as another polysaccharide. The gel of interest can be obtained by controlling the amount of chemical modification of the backbone but also by blending the native polysaccharide with the modified polysaccharide. This results in a uniform material with feature such as stiffness, thermal gelation and roughness that can be adjusted by incorporating different amounts of each polysaccharide.

The ease of control of the physical properties enables the design of an environment, which is mechanically similar to natural human tissue but also biologically neutral since the polysaccharide (in particular agarose) does not interact with cells. In case it is desired that cells interact with the material, biological ligands that are recognized by cells have to be grafted on the polymer backbone.

The peptide sequence can be attached to the modified polysaccharide by click chemistry, whereby either azide or the alkyne moiety is coupled to the modified polysaccharide and the other moiety is coupled to the peptide sequence.

Scheme 2

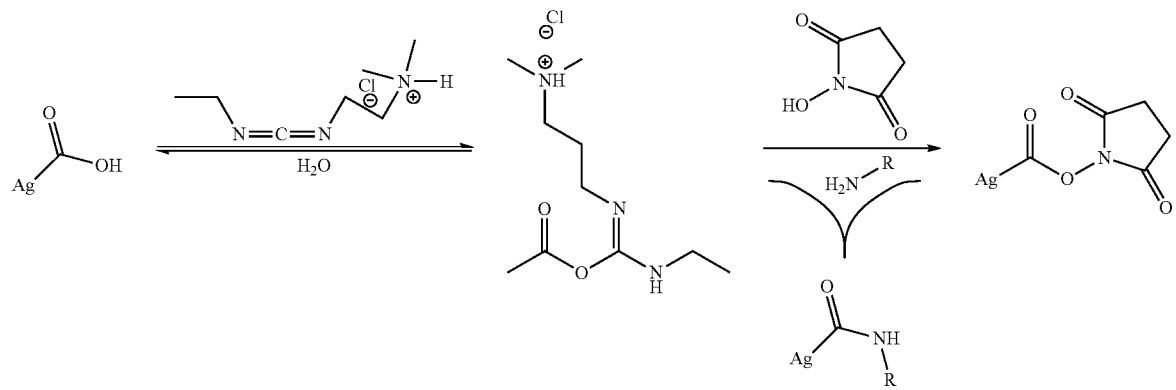

Scheme 2

The second approach has been made with DNA coupling that enables an easier manipulation for the final user. An oligo-DNA strand can be coupled to the polymer backbone with the complementary oligo-DNA strand that has been previously chemically bound to the peptide of interest. This way of binding is for the final user a step forward to a fully tunable system, where the mechanical properties can be adjusted by mixing two components (native with modified polysaccharide) and the biological signal incorporated to the backbone polymer by adding a component to the system (the complementary oligo-DNA strand bounded to the peptide of interest).

In a preferred embodiment the matrix can be used as a scaffold of living cells in order to grow cells in a three-dimensional structure which resembles the natural environment. Cells, preferably human cells, are preferably selected from the group consisting of chondrocytes, osteoblasts, osteoclast, skin epithelial cells, intestinal epithelial cells, corneal epithelial cells, astrocytes, neurons, oligodentrocytes, smooth muscle cells, endothelial cells, cardiomyocytes, pancreatic islet cells, kidney epithelial cells, embryonic stem cells, pluripotent stem cells; or naïve cells obtained from umbilical cord.

The matrix of the present invention can be further used for experimental purposes since the interaction of cells and its understanding gains more and more importance in many fields of biological research. Alternatively, the matrix can be used in order to produce artificial tissues. It is for example possible to grow the cells as described above in order to produce artificial three-dimensionally linked tissues which can be used as implant for the curing of various defects. It is for example possible to produce homologous bone structures by cultivating osteoblasts and/or osteoclasts in the matrix as described herein. Alternatively, artificial skin or cartilage can be produced. Since the material is well compatible with the immune system, no unexpected allergic reactions can be expected. This is especially true when homologous cells are used for the preparation of artificial tissues.

The matrix of the present invention can be implanted in mammalian body cavities both in the presence and in the absence of growth factors. These cavities can be with or without cells.

In a particularly preferred embodiment the matrix of the present invention is used as a regenerative implant. Such a regenerative implant is produced in vitro by using the matrix as a scaffold for the tissues, which grow three-dimensionally in vitro. After the implant has reached the desired structure it can be implanted into a patient. Since the form of such an implant can be precisely designed by using the appropriate stiffness and viscosity or the required modulus usually in the first step the matrix is formed as a scaffold having the desired form. This matrix may be present in various forms. Sheets with a defined thickness are incubated with dermal cells and artificial skin can be produced thereby. Tubes having a well-defined diameter are incubated with suitable cells, which form blood vessels like endothelial cells in order to produce artificial arterioles or venules.

It is possible to form tubular structures, which are brought into contact with such type of cells, which form blood vessels. Alternatively, the matrix may have the form of a disc and the matrix will be brought into contact with cells, which form cartilage tissues. Since the mechanical properties like stiffness, rigidity and viscosity of the matrix can be controlled by selecting the appropriate ratio of modified polysaccharide: unmodified polysaccharide, in particular modified agarose: unmodified agarose, the properties can be regulated very precisely. It is a further advantage of the present invention that the three-dimensional structure of the tissue is given by the matrix. Therefore, thickness, length or any other desired form of the matrix can be prepared by using a suitable form or mold. For medical purposes it is preferred to sterilize the polysaccharide. This can be done either by appropriate chemicals or more preferred by heat treatment or by radiation.

The methods used to sterilize the polysaccharide are not particularly limited. As a suitable chemical agent for sterilization ethylene oxide is advantageously used. Polysaccharides can also be sterilized by a treatment with ionizing radiation, such as x-rays, gamma-radiation or with electronic beam. It is however, particularly preferred to carry out sterilization of polysaccharides by a heat treatment. Such heat treatment is advantageously carried out in an autoclave at a temperature of ca. 121° C. and pressure of 110 kPa whereby the sterilization time of at least 15 min is usually sufficient. Alternatively, sterilization can be carried out by a filtration using a sterile filter with pore size of less than 0.5 µm, preferably less than 0.3 µm.

After the matrix has been brought into the desired form and the form has been sterilized it can be brought into contact with the desired cells, preferably in the appropriate medium, which contains the desired growth factors. Depending on the type of cell, which grows on the matrix, appropriate cytokines are added. It is also possible to add sequentially two different types of cells in order to form an matrix wherein tissues have been grown which resemble the part of the body which should be replaced or supported as far as possible. Such matrices wherein tissue cells have been grown to form tissues can be used as regenerative implants in the treatment of humans. It is possible to produce by using the matrix of the present invention regenerative implants, which can be used as artificial skin, as artificial blood vessels or for the replacement of nerve tissues. It is also possible to produce mucosal tissues or parts of the eye, in particular artificial lenses. A particular advantage of the present invention is that the matrix has superior optical quality, which means that the matrix can be completely clear. In particular, a matrix containing a modified polysaccharide having a high modification degree has a particularly high transparency. This is extremely important for forming artificial cornea and/or lenses.

In another embodiment of the present invention the matrix can be used as a plastic surgery implant for reconstructive and cosmetic surgery in diverse body regions: in the facial region such as a nose, a forehead, a jaw, a cheek but also in a breast, a hip, a calf and the like. For example, in case of the nose correction, because the small implant is inserted between the nasal bone and the periosteum, the material of the implant need to be sufficiently stiff so that the implant does not deviate from its original position. However, in case of the breast correction, a relatively large implant and soft implant is employed.

The mechanical properties of the matrix such as stiffness and roughness can be adjusted as outlined above. Thus, the properties of the plastic surgery implant comprising the matrix can be conveniently adjusted depending on the intended purpose and used in a wide variety of body regions.

In yet another embodiment of the present invention the matrix can be used for producing controlled drug release formulations of pharmaceutically active components. By varying the mechanical properties of the matrix the controlled drug release formulation can be tailored to the desired site of application to ensure compliance matching and viscosity can be used to tailor drug release. If for example the matrix is very viscous, pharmaceutical agents, which are included within the matrix will be delivered after implantation into the body very slowly.

Charged modified polysaccharides in accordance with the present invention in the matrices in accordance with the present invention may be successfully used to modulate the release of growth factors as a function of the interaction of the growth factor with the charged moieties at the polysaccharide.

As an example, FGF-2 release from hydrogels modified in accordance with the present invention has been studied and it has been found that the release of FGF-2 can be adjusted through the extent and type of modification. In general, the release of FGF-2 from modified hydrogels is increased compared to polysaccharide hydrogels without the modification and the release kinetics can be tuned through type and degree of modification. In a CAM assay, hydrogels loaded with FGF-2 induced an increase of angiogenesis whereas unmodified control samples under identical conditions did not exhibit a respective change. The modified polysaccharides in accordance with the present invention are in general non-inflammatory.

In a further embodiment of the present invention the matrix can be used with pharmaceutically active agents like growth factors, insulin, biologically active peptides, chemokines, cytokines, steroids, antibiotics, analgesics and anti-inflammatory agents or anti-cancer drugs.

In a further embodiment the matrix can also be used for diagnostic purposes by including imaging agents as e.g. magnetic resonance imaging (MRI) contrast agents, computed tomography (CT) contrast agents, fluorescent imaging probes or radionuclei. By including those agents into the matrix and applying thereafter the matrix to the human body the agents are trapped into the matrix and can be released in a controlled manner by adjusting the properties of the matrix like viscosity, stiffness and form which depends on the intended use.

It is also possible to include into the matrix cells, which form a tissue and pharmaceutically active agents.

Another embodiment of the present invention relates to the use of the matrix as a food additive. Such food additive is useful for the preparation of foods, drinks or seasonings. Preferably, the foods, drinks or seasonings contain 0.1 to 30 wt.-% of the matrix polysaccharide relative to the total weight of said food, drink or seasoning, more preferably they contain 0.5 to 25 wt.-% of the matrix polysaccharide, whereby the content of 1 to 20 wt.-% of the matrix polysaccharide is particularly preferred. The foods, drinks or seasonings containing the matrix of the present invention are not specifically limited. For instance, examples of such food include the following: products of processed cereal (e.g., wheat flour products, starch products, premixed puddings, jam, buckwheat noodle, wheat-gluten bread, jelly bears, gelatin noodle and packed rice cake), products of processed fat and oil (e.g., margarine, salad oil, mayonnaise and dressing), products of processed soybeans (e.g., tofu, miso and fermented soybean), products of processed meat (e.g. brawn and sausage), processed marine products (e.g., frozen fish, fish paste and fish fingers), dairy products (e.g., raw milk, cream, yogurt, butter, cheese, condensed milk, powdered milk and ice cream), products of processed vegetables and fruits (e.g., paste, jam, pickle), and the like.

Because the components of the matrix have a sufficient chemical stability, the process for producing the food, drink or seasoning containing the matrix of the present invention is not limited to a specific one. Any processes including cooking, processing and other generally employed processes for producing a food, drink or seasoning can be used and the components of the matrix may be added before, during or after the cooking or processing, either separately or in a form of a pre-prepared matrix.

Importantly, the amount as well as the properties of the matrix employed producing the food, drink or seasoning can be adapted according to the desired consistency of the resulting products. For instance, preparation of jelly bears typically requires a higher content of the matrix polysaccharides than preparation of a pudding.

The matrix of the present invention can also be used as a pharmaceutical excipient, for instance for the preparation of oral pharmaceutical formulations.

In another embodiment the matrix of the present invention is used as a component of cosmetic compositions such as make-up, blush, lipstick, eyeshadow, antiperspirants, deodorants and concealer. The cosmetic compositions comprise 0.1 to 50 wt.-% of matrix polysaccharide, preferably 0.5 to 30 wt.-% of matrix polysaccharide, even more preferred 1 to 25 wt.-% and particularly preferred 2 to 20 wt.-%. The content of matrix polysaccharide is chosen according to the desired mechanical properties of the cosmetic compositions. Preferably, the cosmetic compositions are characterized by being single phase.

Preferably, the cosmetic compositions are solid or semi-solid at temperature of 25° C. and have such a consistency that they can be molded into the form of a stick. For this purpose, the compositions can be heated until molten and then poured into a mold and cooled. Alternatively, the compositions are capable of being formed into sticks, but are poured into pans or other types of cake or cream forms to deliver certain consumer benefits. For example, an eyeshadow composition may be molded in the stick form, but usually it is desired to pour it into a pan for a more convenient use from a consumer standpoint.

The physical properties of the resulting cosmetic compositions can be conveniently adjusted by an appropriate choice of the matrix components and by their amount in the composition.

In another embodiment the matrix of the present invention is used as a material for industrial purposes, in particular as for dispersion control, for conditioning of liquids and as a lubricant. Because the properties of the matrix, such as stiffness and temperature of gelation can be conveniently tuned by adapting the modification degree of the modified polysaccharide, their matrix of the present invention is suitable for a wide range of industrial applications.

The concentration of the polysaccharide components of the matrix in the aqueous solution typically ranges from 1 to 4 wt.-%, particularly preferred from 1 to 3 wt.-%. In a particularly preferred embodiment the concentration of the polysaccharide components of the matrix in the aqueous solution ranges from 1 to 2 wt.-%. It is even more preferred that this concentration is about 2 wt.-%.

The aqueous solution can further contain other compounds, such as salts or proteins, in particular water-soluble proteins.

DESCRIPTION OF THE DRAWINGS

FIG. 1 shows ESEM images of 2% w/v freeze dried gels of the modified polysaccharides;

FIG. 2: shows AFM phase images of the surface of 2% w/v wet hydrogels.

METHODS DESCRIPTION a) ESEM

ESEM images were obtained with a ref agarose gels. 2% w/v solutions were prepared and 2 ml of these solutions were freeze-dried for 24 hours under 0.1 mbar vacuum in a 5 ml glass vial. The samples were vertically cut and the inside of the sample was imaged at different magnification.

b) AFM

AFM images were obtained with a scanning probe microscope Veeco Dimension 2100. The samples were prepared on a 3 mm microscopic glass holder that was previously passivated. The glass slide was washed with 0.1 M NaOH solution and dried in the oven. The dry slides were then passivated with a few drops of dichloromethylsilane. Two slides were sandwiched together to have a uniform passivation. After 10 min the slides were washed with water and the excess of dichloromethylsilane was washed away with soap after what the slides were dried. Slides side was prepared in a hydrophobic way. Agarose samples were prepared as 2% w/v gels and 25 µl of the obtained solution was poured on an unmodified glass slide. A dichloromethylsilane passivated slide was then adjusted on top of the solution. Slides of 0.5 mm were put as spacers between the hydrophobic and the normal glass slide, the whole montage was then allowed to gel for 30 min at 4° C. The upper slide (hydrophobic) was after that removed and a thin layer of agarose gel was obtained. This gel was then allowed to stabilize at room temperature for 30 min before measurement in order to avoid any shrinkage or dilatation of the gel during the measurement.

c) Molecular Dynamic Simulations

MD simulations were done using the Desmond package of the Maestro, Version 8.5 from Schrödinger. Initial conformation was been obtained from the X-ray structure of the agarose that was downloaded from the protein database (PDB) library. Modified agarose was drawn from the PDB file directly inside the Maestro software. Implicit water model was build using the Desmond tool, resulting in a 10 Å square box build by following the TIP3 solution model. The simulations were run in the model NPV at 300° K at atmospheric pressure for 15 ns. Analysis of the results was done using the VMD software and the tools available in the standard package.

EXAMPLES

Example 1

Synthesis of Brominated Agarose 500 mg of agarose, 580 mg of N-Bromosucciniomide, 850 mg triphenyl phosphine and 15 ml of dry dimethyl formamide were charged into a flame dried round bottom flask under Argon and the reaction mixture was stirred for 1 h at 50° C. The reaction mixture was dialyzed against water for two days using a 12,000-14,000 MWCO (molecular-weight cut-off) membrane, and thereafter freeze dried.

Example 2

Synthesis of Sulfated Agarose 20 ml pyridine were cooled in an ice bath and 2 ml of chlorosulfonic acid were very slowly added. 1 g of Agarose was swollen in 70 ml of formamide for 45 min and then added to the chlorosulfonic acid-pyridine mixture under continuous stirring. Thereafter stirring was continued for 4 hours at a temperature of 85° C.

The reaction mixture was neutralized with sodium hydroxide (2 molar) and thereafter precipitated in ethanol and centrifuged three times with ethanol and cleaned with distilled water. Thereafter the system was dialyzed against water using a membrane with a molecular-weight cut-off of 12,000-14,000.

$^1$H-NMR, $^{13}$C-NMR and FTIR showed partial modification of the primary hydroxyl group of the agarose with sulfate groups.

Example 3

Synthesis of Phosphated Agarose 7.5 mg urea were dissolved in 7.5 ml dimethyl sulfoxide at a temperature of 95° C. under argon atmosphere until a clear solution was obtained. 200 mg of Agarose was added and the solution was heated to 110° C. and reflux while maintaining the protective argon atmosphere. After dissolution of the agarose, 1.25 ml of phosphoric acid (85 wt %) was added and the mixture was stirred for three hours under argon.

Thereafter, the reaction mixture was cooled to room temperature and 100 ml of methanol (analytical grade p.a.) was added. The pale yellow powder formed was filtered and washed three times with 50 ml of methanol. The product was dialyzed against water for two days against a membrane with a molecular weight cut-off of 3500, and freeze dried. NMR and DMSO confirmed partial modification of the primary hydroxyl group in the agarose by phosphate groups.

FIG. 1 show the ESEM pictures of 2% w/v freeze dried gels of the products obtained in Examples 1 to 3 whereas FIG. 2 shows the AFM phase surface images of the respective products obtained in examples 1 to 3.

Example 4

FGF-2 Release from Modified Hydrogels

Hydrogels comprising the modified agarose as obtained in examples 2 and 3 showed a sustained release of FGF-2 over a period of seven days. The FGF-2 release in vitro was dependent on the nature of the functional group in the backbone. The phosphated agarose showed a higher release rate in vitro and the kinetics of the release can be tuned through the degree of modification and the nature of the group. FGF-s in the release study was loaded in the 2% w/v gels and its release into PBS was monitored over one week. Released FGF-2 was quantified using ELISA.

In an in vivo CAM assay hydrogels loaded with FGF-2 induced an increase of angiogenesis while retaining the GFG-2 activity. Negative controls did not exhibit such changes. The CAM assay was performed by loading gels with FGF-2 and the number of macro blood vessels reaching the gel was manually counted at different points in time.

Example 5

Cytocompatibility of Brominated Agarose as Obtained in Example 1

The viability of HeLA and MDA-MB231 cancer cells was assessed by MTT assay. Both cell lines proliferated normally upon treatment with media that was exposed to the brominated agarose hydrogel which is indicative of the absence of appreciable amounts of free bromide ions which are known to be toxic to cells.

The foregoing examples show that modified polysaccharides in accordance with the present invention show several important characteristics that make them highly suited for a large variety of applications, in particular also as synthetic extracellular matrix (ECM) material. The materials show a tunable spectrum of mechanical properties, a modulated affinity towards soluble signals and a well-defined macrostructure as well as a good cytocompatibility.

The invention claimed is:

1. A matrix comprising a modified primary hydroxyl groups containing polysaccharide comprising repeating disaccharide units wherein in at least part of the disaccharide units the primary hydroxyl group is replaced by functional groups selected from F, Cl, Br, or I or functional groups comprising phosphorus atoms.

2. The matrix according to claim 1, characterized in that the functional group is F, Cl, Br, or I.

3. The matrix according to claim 1, characterized in that the functional group is a phosphonate or phosphate group.

4. The matrix in accordance with claim 1, comprising halide groups in combination with phosphonate or phosphate groups.

5. The matrix in accordance with claim 1, additionally comprising unmodified polysaccharides.

6. The matrix in accordance with claim 5, characterized in that the unmodified polysaccharide is agarose.

7. The matrix in accordance with claim 5, characterized in that the unmodified polysaccharide is selected from the group consisting of a member of the carrageenan family, hyaluronic acid, heparin sulfate, dermatan sulfate, chondroitin sulfate, alginate, chitosan, pullulan and agarose.

8. The matrix in accordance with claim 1, characterized in that the modified polysaccharide is agarose.

9. The matrix in accordance with claim 1, characterized in that the polysaccharide is of natural origin.

10. The matrix in accordance with claim 1, characterized in that the modified polysaccharide is selected from the group consisting of a member of the carrageenan family, hyaluronic acid, heparin sulfate, dermatan sulfate, chondroitin sulfate, alginate, chitosan, pullulan and agarose.

11. The matrix according to claim 1, for use as scaffold for living cells or for use as a regenerative implant comprising living cells selected from the group consisting of chondrocytes, osteoblasts, osteoclasts, skin epithelial cells, intestinal epithelial cells, corneal epithelial cells, astrocytes, neurons, oligodentrocytes, smooth muscle cells, endothelial cells, cardiomyocytes, pancreatic islet cells, kidney epithelial cells and naïve cells obtained from umbilical cord or for use as a plastic surgery implant or for use as a controlled drug release implant.

12. Food additive comprising the matrix of claim 1.

13. Cosmetic composition comprising the matrix of claim 1.

14. Lubricant comprising the matrix of claim 1.

15. A method for the conditioning of liquids wherein the matrix of claim 1 is used.

16. Modified primary hydroxyl groups containing polysaccharides, wherein at least 5% of the primary hydroxyl groups have been converted to halide groups.

17. Hair-care products comprising modified polysaccharides in accordance with claim 16, optionally blended with unmodified polysaccharides.

18. Modified primary hydroxyl groups containing polysaccharides in accordance with claim 16 wherein the polysaccharide is agarose.

19. Modified agarose wherein at least 5% of the primary hydroxyl groups have been converted to phosphonate or phosphate groups.

* * * * *